US009421226B2

(12) United States Patent
Bartolozzi et al.

(10) Patent No.: US 9,421,226 B2
(45) Date of Patent: Aug. 23, 2016

(54) EXERCISE PHYSIOLOGY ELECTROLYTE MANAGEMENT

(71) Applicant: Heat Sport Sciences, Inc., Malvern, PA (US)

(72) Inventors: Arthur R. Bartolozzi, Philadelphia, PA (US); Sandra Fowkes Godek, Kennett Square, PA (US)

(73) Assignee: Heat Sport Sciences, Inc., Malvern, PA (US)

(*) Notice: Subject to any disclaimer, the term of this patent is extended or adjusted under 35 U.S.C. 154(b) by 0 days.

(21) Appl. No.: 14/414,735

(22) PCT Filed: Jul. 18, 2013

(86) PCT No.: PCT/US2013/051055
§ 371 (c)(1),
(2) Date: Jan. 14, 2015

(87) PCT Pub. No.: WO2014/074181
PCT Pub. Date: May 15, 2014

(65) Prior Publication Data
US 2015/0174162 A1 Jun. 25, 2015

Related U.S. Application Data

(60) Provisional application No. 61/672,928, filed on Jul. 18, 2012.

(51) Int. Cl.
| | |
|---|---|
| A61K 33/20 | (2006.01) |
| A61K 33/14 | (2006.01) |
| A61K 31/047 | (2006.01) |
| A61K 31/70 | (2006.01) |
| A61K 31/7016 | (2006.01) |
| A61K 9/00 | (2006.01) |
| A23L 1/304 | (2006.01) |
| A23L 2/39 | (2006.01) |
| A61K 31/7004 | (2006.01) |
| A61K 33/00 | (2006.01) |

(52) U.S. Cl.
CPC .............. *A61K 33/20* (2013.01); *A23L 1/304* (2013.01); *A23L 2/39* (2013.01); *A61K 9/0095* (2013.01); *A61K 31/047* (2013.01); *A61K 31/70* (2013.01); *A61K 31/7004* (2013.01); *A61K 31/7016* (2013.01); *A61K 33/00* (2013.01); *A61K 33/14* (2013.01)

(58) Field of Classification Search
None
See application file for complete search history.

(56) References Cited

U.S. PATENT DOCUMENTS

| | | | |
|---|---|---|---|
| 3,596,629 A | 8/1971 | English | |
| 2003/0201192 A1 | 10/2003 | Prince et al. | |
| 2007/0059362 A1 | 3/2007 | Rau | |
| 2007/0083095 A1 | 4/2007 | Rippo et al. | |
| 2008/0050451 A1* | 2/2008 | Mabry | C12Q 1/40 424/600 |
| 2008/0089993 A1 | 4/2008 | Hwang et al. | |
| 2008/0234600 A1* | 9/2008 | Marsh | A61B 5/01 600/549 |
| 2008/0292499 A1 | 11/2008 | Murray et al. | |
| 2009/0117224 A1 | 5/2009 | Robergs | |
| 2011/0262596 A1 | 10/2011 | Murray et al. | |
| 2011/0280988 A1* | 11/2011 | Ivy | A23L 1/296 426/2 |

FOREIGN PATENT DOCUMENTS

WO   WO 2014/074181   5/2014

OTHER PUBLICATIONS

Baker et al, "Comparison of Regional Patch collection vs. Whole Body Washdown for Measuring Sweat Sodium and Potassium Loss During Exercise", J. Appl. Physiol, Jun. 18, 2009, 107, 887-895.
Eichner, E.R., "Heat Cramps in Sports", Current Sports Medicine Reports: Pearls and Pitfalls, Jul./Aug. 2008, 7(4), 178-179.
Fowkes et al, "Sweat Rates, Sweat Sodium Concentrations, and Sodium Losses in 3 Groups of Professional Football Players", Journal of Athletic Training, Aug. 2010, 45(4), 364-371.
Godek et al, "Core Temperature and Percentage of Dehydration in Professional Football Linemen and Backs During Preseason Practices", Journal of Athletic Training, Mar. 2006, 41(1), 57-66.
Godek et al, "Hydration and Core Temperature in a Football Player during Preseason: A Case Study", Athletic Therapy Today, Jul. 2004, 9(4), 64-70.
Godek et al, "Hydration Status in College Football Players During consecutive Days of Twice-a-Day Preseason Practices", The American Journal of Sports Medicine, Jun. 2005, 33(6), 843-851.
Godek et al, "Sweat Rate and Fluid Turnover in American Football Players Compared With Runners in a Hot and Humid Environment", British Journal of Sports Medicine, Jun. 2005, 55(267), 1-7.

(Continued)

*Primary Examiner* — Susan Tran
(74) *Attorney, Agent, or Firm* — Baker & Hostetler, LLP

(57) ABSTRACT

The present invention provides methods for maintaining electrolyte balance and hydration in a person habituated to strenuous physical exertion by assaying perspiration generated by the person under conditions of strenuous physical exertion to determine the volume of perspiration as a function of duration of exertion and the sodium content of the person's perspiration during strenuous physical exertion The person is assigned to one of a plurality of groups of individuals, each group differing in the amount of sodium present in the perspiration and having a unique rehydration solution. The invention also provides for a set rehydration compositions, each member of the set comprising sodium and chloride differing from the weight percentage of sodium in the other members of the set and each member of the set being perceptually labeled to distinguish that member from the other members of the set by one of the human senses.

55 Claims, No Drawings

(56) References Cited

OTHER PUBLICATIONS

Godek et al, "Thermal Responses in Football and Cross-Country Athletes During Their Respective Practices in a Hot Environment", Journal of Athletic Training, Sep. 2004, 39(3), 235-240.

Godek, S.F. and Bartolozzi, A.R., "Changes in Blood Electrolytes and Plasma Volume in National Football League Players During Preseason Training Camp", Athletic Training & Sports Health Care, 2009, 1(6), 259-266.

Hamouti et al, "Sweat Sodium Concentration During Exercise in the Heat in Aerobically Trained and Untrained Humans", Eur. J. Appl. Physiol., 2011, 111, 2873-2881.

International Patent Application No. PCT/US13/51055: International Search Report and Written Opinion dated Jul. 11, 2014, 29 pages.

Maughan et al, "Fluid and Electrolyte Intake and Loss in Elite Soccer Players During Training", Intl. Journal of Sport Nutrition and Exercise Metabolism, 2004, 14, 333-346.

Maughan et al, "Water Balance and Salt Losses in Competitive Football", Intl. Journal of Sport Nutrition and Exercise Metabolism, Dec. 2007, 17, 583-594.

Maughan, Ron J., "Fluid and Electrolyte Loss and Replacement in Exercise" Journal of Sports Sciences, 1991, 9(S1), 117-142, Published Online: Nov. 14, 2007.

Montain, S.J, "Hydration Recommendations for Sport 2008", Curr. Sports Med. Rep., Jul./Aug. 2008, 7(4), 187-192.

Palacios et al, "Sweat Mineral Loss From Whole Body, Patch and Arm Bag in White and Black Girls", Nutrition Research, Mar. 2003, 23, 401-411.

Shamsuddin et al, "Changes in the Index of Sweat ion Concentration With Increasing Sweat During Passive Heat Stress in Humans", Eur. J. Appl. Physiol., Jun. 2005, 94, 292-297.

Shirreffs, S.M. and Maughan, R.J., "Whole Body Sweat Collection in Humans: An Improved Methods with Preliminary Data on Electrolyte Content" The American Physiological Society, Jan. 1, 1997, 82(1), 336-341.

Von Duvillard et al, "Sports Drinks, Exercise Training, and Competition", Curr. Sports Med. Rep., Jul./Aug. 2008, 7(4), 202-208.

* cited by examiner

EXERCISE PHYSIOLOGY ELECTROLYTE MANAGEMENT

CROSS-REFERENCE TO RELATED APPLICATIONS

This application is the National Stage of International Application No. PCT/US2013/051055, filed Jul. 18, 2013, which claims the benefit of U.S. Provisional Application No. 61/672,928 filed Jul. 18, 2012, the disclosures of which are incorporated herein by reference in their entireties.

BACKGROUND

Individuals who perform intense physical exertion have long strived to improve their physical performance and recover faster. Individuals, such as professional athletes, military personnel, construction workers, and the like perform intense physical exertion on a regular basis. It is important these individuals are able to recover quickly and maintain maximum performance over an extended period of time. However, proper exercise physiological management is still lacking. Current methods fail to adequately provide electrolytes, hydration and carbohydrates in suitable proportions. Individuals continue to fail to reach maximum performance and suffer from heat illnesses, which can result in death.

The body must have proper balance of electrolytes and hydration to function properly. However, during intense physical exertion, the body is thrown out of balance. The average adult has a metabolic rate between 60 and 70 kcal/h at rest. However, during physical activity, metabolic rate increases to as much as 1000 kcal/h. The excess heat produced by the body during physical exertion is dissipated by a variety of means including radiation, conduction, convection and evaporation. In particular, evaporation occurs by vaporization of perspiration and is the most efficient means for dissipating the excess heat. Evaporation cools the body due to the latent heat of evaporation of water from the perspiration.

Perspiration contains several components including water, lactate, urea, potassium, calcium, magnesium, sodium and chloride. High rates of perspiration can lead to dehydration and loss of vital electrolytes, especially sodium, that are necessary for proper body function. In particular, appropriate electrolyte balance is required to maintain normal cell membrane potential both at rest and during activity, and therefore proper nerve and muscle function. The nervous system requires sufficient sodium levels for proper electrical signal transmission. Constant nerve impulses are required for a muscle to contract. The sodium and potassium are responsible for membrane depolarization that results in acytlecholine release from the terminal nerve endings and ultimately $Ca^{++}$ release from the sarcoplasmic reticulum within the muscle cell. This subsequent increase in intracellular concentration of $Ca^{++}$ causes muscle contraction. An inadequate balance of these electrolytes contributes to poor physical performance and may threaten health or even life.

Sodium loss can lead to low serum sodium concentration, hyponatremia. Hyponatremia can cause nausea and vomiting, difficulty concentrating, confusion, headache and in extreme cases, seizures and death (exercise associated hyponatremic encephalophathy—or brain swelling due to acute overdrinking). Furthermore, as discussed above, sodium is vital for proper muscle and nerve function. Another aspect of hyponatremia can lead to the inability to rehydrate, especially after several days of intense physical exertion. Sodium is required for the body to retain water. An individual can have difficulty retaining water if the individual does not properly replenish his sodium levels.

Dehydration is a process whereby an individual suffers from water loss without proper replenishment. An individual can exceed 4.0 liters of water per hour during intense physical activity. Dehydration can cause fatigue, muscle weakness, poor concentration, headaches, dizziness, decreased metabolism, increased heart rate, increased respiration, decreased urination, increased body temperature, extreme fatigue, muscle cramps, headaches, nausea, muscle spasms, vomiting, increased pulse, decrease in vision, confusion, chest and abdominal pain. In extreme circumstances, seizures, unconsciousness and death can occur from dehydration.

Failure of the body properly to thermoregulate or the lack of replenishment of vital electrolytes can lead to exertional heat illness. Exertional heat illnesses such as exertional heat stroke can occur if the body fails to properly thermoregulate itself because body temperature continues to rise. Examples of exertional heat illness include localized muscle cramps, systemic cramps, heat syncope (orthostatic dizziness), heat exhaustion, heat stroke, hyperthermia, hypovolemic hyponatremia, exercise associated hyponatremia and other syndromes. In some instances, these conditions can cause death. All persons can suffer exertional heat illnesses. However, specific groups of individuals, such as professional athletes and military personnel, are more prone to suffer from exertional heat illnesses due to environmental factors, uniforms and equipment.

Thermoregulation is a complex process that includes interaction between the central nervous system, cardiovascular system, renal and endocrine systems as well as the integumentary system. Factors which can inhibit the body's ability to properly thermoregulate include dehydration prior to physical exertion (known as hypohydration), clothing or environmental factors that inhibit evaporation of perspiration, viral or bacterial illness, history of heat illness, high body mass index, physical exertion unmatched by physical conditioning, overzealousness, lack of acclimatization, genetic predisposition factors such as malignant hyperthermia or exertional sickling and the use of alcohol, drugs, or medications. Even though it has been known that proper electrolyte replacement and hydration aides in physical performance, recovery and prevention of exertional heat illnesses, current replenishment systems still fail to obtain good results. Furthermore, it is still unknown the exact role electrolyte imbalance plays in many exertional heat illnesses. For example, while it has been shown that sodium chloride can help in the prevention of heat cramps, the exact cause of cramping is still unknown (Eichner, E. R., Sports Medicine Pearls and Pitfalls: Heat Cramps in Sports, Current Sports Medicine Reports, 2008, 7(4), 178-179). Individuals who take part in high intensity physical activity which results in high amounts of perspiration loss are encouraged to consume sports drinks to replenish water and electrolyte loss. It is known that individuals can have very different perspiration rates and compositions. The concentration of sodium in perspiration can vary from about 50 mg/L to about 2500 mg/L depending on the individual. Meanwhile, the concentration of potassium remains relatively constant. It is known that an individual's sodium concentration will be at the highest prior to the individual's becoming heat acclimated to a particular environment. As the individual becomes acclimated to the heat environment, his sodium concentration will decrease slightly. This is due to greater reabsorption of sodium in the sweat ducts.

Additionally, the perspiration rate can vary between about 0.2 liters/hour and 4.0 liters/hour. Depending on an individual's perspiration rate and sodium loss concentration, an individual can lose a significant amount of sodium during intense physical exertion. The typical sports drink, which contains approximately 100 mg of sodium, 30 mg potassium, and 15 grams of sugar per 240 mL of water, may not be appropriate for all individuals. For example, an individual with a high a perspiration rate and high sodium concentration could lose 1 liter of water, 2000 mg of sodium and 200 mg of potassium during intense physical activity. An individual would be required to drink twenty servings of this sports drink. This would result in an individual consuming 4.8 liters of water, 2000 mg of sodium, 600 mg of potassium and 300 grams of sugar (1200 kcal). In other situations, a higher loss of sodium could result in even higher consumption of water and calories. An individual would suffer from hyperhydration and hyperkalemia, while also consuming 1200 kcal of sugar. Hyperkalemia could cause muscle weakness, malaise, palpitations, and hyperventilation. Extreme hyperkalemia can cause fatal abnormal heart rhythms. On the other hand, certain individuals may have a low perspiration rate and low sodium concentration. For example, an individual may lose 0.200 liters of water, 120 mg of sodium and 25 mg of potassium. Again, the average sports drink will not properly replenish electrolytes and hydration. It has been suggested that rehydration drinks should have a sodium concentration similar to that of sweat of an individual (Maughan, R. J., Fluid and Electrolyte Loss and Replacement in Exercise, Journal of Sports Sciences, 1991, 9, 117-142). However, this is an overly simplistic solution and fails to address the problem of proper exercise physiology management. Current methods fail to address the complexity of the human body in this regard and the variance between individuals.

SUMMARY

The present invention is directed to methods for improving exercise physiology electrolyte management. Certain of the embodiments of this invention are useful for participants habituated to strenuous physical exertion. For example, the present invention will benefit military personnel, who have to participate in intense physical exercise on an almost daily basis during training. Additionally, athletes in nearly all sports engage in intense physical exercise during training and competition. These examples are not limiting and a person of ordinary skill in the art will understand that many other populations also will benefit from the present invention. Certain exemplifications of the invention will benefit groups of persons who, as a group, exert intense physical exercise, while other aspects are directed to individuals.

In accordance with some embodiments of this invention, a person or persons are evaluated as to his, her or their perspiration rate during exertion together with one or more chemical constituents of such perspiration. Other incarnations of this invention include assigning a person or persons to one of a plurality of groups of individuals, with each group differing in the amount of sodium present in the perspiration during strenuous physical exertion of individuals assigned to that group. Additionally, some embodiments of this invention include providing to a person or persons after a period of strenuous physical activity a rehydration solution designed for individuals assigned to the group to which the person is assigned. The rehydration solution includes water, sodium and chloride. The rehydration solution may be provided in an amount comprising from about 50 volume percent to about 125 volume percent of the amount of perspiration generated by the person over the time period of strenuous physical exertion. Preferably, the rehydration solution may be provided in an amount comprising from about 65 volume percent to about 100 volume percent of the amount of perspiration generated by the person over the time period of strenuous physical exertion. In some embodiments, the rehydration solution may include from about 75 percent to about 125 percent by weight of the sodium content of the perspiration generated by the person over the time period and having at least about 75 percent by weight of chloride compared to the chloride content of the perspiration generated by the person over the time period. Preferably, the rehydration solution may include from about 85 percent to about 115 percent by weight of the sodium content of the perspiration generated by the person over the time period and having at least about 125 percent by weight of chloride compared to the chloride content of the perspiration generated by the person over the time period.

In accordance with other embodiments, a person may determine his total sodium loss during a time period of strenuous physical activity. For example, a person may determine his or her total sodium lost by accounting for sodium lost during urination or sodium gained from any dietary intake. The person may be provided a rehydration solution after a period of strenuous activity and being provided a rehydration solution which may include about 85 percent to about 115 percent by weight of the sodium loss by the person over the time period, with about less than 1 percent of potassium compared to the weight of sodium and at least about 110 percent chloride by weight of the chloride content of the perspiration generated by the person over the time period. Preferably, the rehydration solution which may include about 90 percent to about 110 percent by weight of the sodium loss by the person over the time period, with about less than 1 percent of potassium compared to the weight of sodium and at least about 125 percent chloride by weight of the chloride content of the perspiration generated by the person over the time period In accordance with other exemplars of this invention, a person or persons are evaluated as to his, her or their perspiration rate during exertion together with one or more chemical constituents of such perspiration and further determining the gain of one or more chemical constituents by dietary intake. Additionally, some embodiments of this invention include providing to a person or persons after a period of strenuous physical activity a rehydration solution designed for individuals assigned to the group to which the person is assigned. The rehydration solution may be provided in an amount comprising from about 50 volume percent to about 125 volume percent of the amount of perspiration generated by the person over the time period of strenuous physical exertion. It is preferred the rehydration solution be provided in an amount comprising from about 50 volume percent to about 125 volume percent of the amount of perspiration generated by the person over the time period of strenuous physical exertion. More preferably, the rehydration solution be provided in an amount comprising from about 65 volume percent to about 100 volume percent of the amount of perspiration generated by the person over the time period of strenuous physical exertion. In some incarnations, the rehydration solution may include from about 85 percent to about 115 percent by weight of the sodium lost by the person over the time period and having at least about 100 percent by weight of chloride compared to the chloride content of the perspiration generated by the person over the time period. Preferably, the rehydration solution may include from about 90 percent to about 110 percent by weight of the sodium lost by the person over the time period and having at least about 125 percent by weight of chloride compared to the chloride content of the perspiration generated by the person over the time period.

In accordance with other incarnations of this invention, a set of unitary dosage rehydration compositions is provided. The unitary dosage rehydration composition may include electrolytes, such as sodium and chloride, in certain ratios. The weight percentage of sodium in each member of the set differs from the weight percentage of sodium in the other members of the set by at least about 20 percent. The weight percentage of chloride in each member of the set exceeds the weight percentage of sodium in that member by at least about 40 percent. Each member of the set may be perceptually labeled to distinguish that member from the other members of the set by one of the human senses. For instance, each member of the set can be distinguished from each other by the shape of the container, the color of the container, taste or smell.

The present invention may be understood more readily by reference to the following description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In accordance with this invention, persons habituated to strenuous physical activity are persons who will perform strenuous physical activity on regular basis. It will be understood by one of ordinary skill in the art that "regular basis" is dependent on the individual or group. For instance, professional athletes and military personnel can be classified as persons habituated to strenuous physical activity. These examples are not to be considered limiting and those of ordinary skill in the art will appreciate which person or persons may be classified as persons habituated to strenuous physical activity.

Several methods are suitable for generation and collection of perspiration samples of participants. Collection of perspiration may be collected at any time. It is preferred the perspiration is sampled prior to the participant being acclimated to the environment in which the physical activity will occur. For example, perspiration samples should be collected for military personnel at the onset of deployment to a new environment. Furthermore, it is preferred the perspiration is sampled and collected while the participant is performing his or her normal strenuous physical activity. For example, the perspiration is sampled and collected from a long distance runner while the individual is participating in long distance running.

Materials that absorb perspiration may be affixed to several parts of the body where persons generally perspire prior to the physical exertion. Suitable materials include medical gauze or the like. A person of ordinary skill in the art will appreciate suitable materials for perspiration collection. The absorbent materials may be placed on several locations, including the lower back, upper back, middle back, forearm, chest, stomach, calf, thigh, neck, forehead, bicep, or any area of the body which perspires. Preferably, at least one of the sites selected for collection is the forearm. A person of ordinary skill will appreciate which areas of the body are suitable. A sufficient number of locations on the body should be sampled. At least one site must be sampled. It is preferred three or more sites be sampled. Sampling of a minimum of five sites is most preferred. Preferably, the sample should be collected between 20 minutes and 90 minutes after initiation of physical activity. More preferably, the sample should be collected between 30 and 60 minutes after initiation of physical activity.

Additionally, the collection of perspiration samples may also occur within a laboratory environment. A participant can exercise within a closed environment where all, substantially all or a representative proportion of the perspiration is collected. The participant should attempt to exert approximately the same level of physical activity in which they will typically participate under normal circumstances. A person of ordinary skill in the art will appreciate the appropriate method to collect perspiration for a participant or group of participants. On the other hand, a well-known test for cystic fibrosis involves inducing perspiration by applying a chemical (typically pilocarpine) to an area of skin and applying a weak electrical current. The perspiration is collected and analyzed for the chloride concentration. The sodium content is then approximately determined by correlation with the chloride concentration. However, this method of collecting perspiration samples is not suitable to determine the sodium concentration in perspiration. Pilocarpine stimulation is cholinergic and has been shown to produce very different local sweat rates, especially with repeated exposures (similar to heat acclimatization) compared to even local sweat rates induced thermally. Pilocarpine exposure appears to actually decrease the sensitivity of sweat glands whereas thermal stimulation increases this sensitivity. Sweat electrolyte concentrations will likely change accordingly.

The total volume of water lost during physical activity can be determined from equation (1):

$$\text{TWS} = \text{pre-PAM} - \text{post-PAM} - \text{UL} + \text{FCDPA} \tag{1}$$

Wherein TWS is the total water lost, pre-PAM is the pre-physical activity mass (kg), post-PAM is the post-physical activity mass (kg), UV is the urine volume (liters), and FCDPA is fluids consumed during physical activity (liters). The density of urine and any fluids consumed during physical activity is assumed to be the same as water (1.0 g/mL). It is important for all liquids consumed after initial pre-physical activity weighing, but prior to or during physical activity to be accurately recorded. For optimum results, the individual should be administered pre-measured beverages. Furthermore, participants should attempt to consume the entirety of the beverage (i.e., no spitting or spilling). The beverage may be water or an electrolyte beverage. The perspiration rate may be determined by dividing the total perspiration lost by the length of time of the physical exertion.

Any known method in the art is suitable for assaying the content of perspiration. For example, mass spectroscopy, ion electrodes, flame ionization, high pressure liquid chromatography, gas chromatography, volumetric procedures or the like may be employed to determine the concentration of sodium, chloride, lactate, potassium or the like. A person of ordinary skill in the art will appreciate different assay procedures may be used depending on the chemical constituent assayed. Based upon the perspiration rate and the concentration of a chemical moiety of the perspiration, one of ordinary skill in the art can determine the rate (e.g., mass/time) at which a chemical or chemicals are lost and the total amount of that chemical or chemicals are lost during a period of strenuous physical activity (Fowkes Godek, S.; Peduzzi, C.; Burkholder, R.; Condon, S.; Dorshimer, G.; Bartolozzi, A. R., Sweat Rates, Sweat Sodium Concentrations, and Sodium Loses in 3 Groups of Professional Football Players, Journal of Athletic Training, 2010, 45(4), 364-371).

Based on the individual's total sodium loss (derived from sodium concentration and total volume of perspiration lost), the participant may be assigned to a specific sodium profile level. The sodium profile level is a predefined set of sodium loss levels. The sodium profile level can be defined as increments of a standard number (e.g., 300, 600, 900 etc.). On the other hand, the sodium profile level can be defined by each level increasing by a standard percentage (initial level of 300 followed by increases of 50 percent results in levels of 300, 450, 675, 1012.5 etc.). These examples are not meant to be limiting and one of ordinary skill in the art will appreciate different sets of predefined sodium profile levels are suitable and within the scope of this invention. The individual is assigned based upon the individual's personal perspiration composition. An individual should be assigned to the level in which she most closely resembles. Table 1 illustrates an example of individuals' perspiration profiles assigned to a particular sodium profile levels. For example, an individual with a perspiration loss of 383 mg would be assigned to Level 1, whereas a person with perspiration loss of 1305 mg would be assigned to Level 4. Typically, once an individual determines her individual sodium concentration rate, she will be able to determine the appropriate sodium profile level based upon the amount of time she participates in intense physical exertion. One of ordinary skill in the art will appreciate Table 1 only represents one example and other examples are within the scope of this invention.

TABLE 1

Sodium profile levels

| Level | Sodium profile level | Example of individual sodium loss |
|---|---|---|
| 1 | 300 | 383 mg |
| 2 | 600 | 459 mg |
| 3 | 900 | 965 mg |
| 4 | 1200 | 1305 mg |
| 5 | 1500 | 1650 mg |
| 6 | 1800 | 1777 mg |
| 7 | 2100 | 2205 mg |
| 8 | 2400 | 2320 mg |
| 9 | 2700 | 2821 mg |
| 10 | 3000 | 3100 mg |
| 11 | 3300 | 3444 mg |
| 12 | 3600 | 3605 mg |

TABLE 1-continued

Sodium profile levels

| Level | Sodium profile level | Example of individual sodium loss |
|---|---|---|
| 13 | 3900 | 4005 mg |
| 14 | 4200 | 4201 mg |
| 15 | 4500 | 4668 mg |

The participant may be provided a rehydration solution after a period of strenuous physical activity. The rehydration solution would have a total volume between about 50 percent and about 125 percent of the total water lost during physical activity. It is preferred the total volume should be about between 65 percent and 100 percent of the total water lost during physical activity. Typically, individuals will replace about 60 percent or more of water lost immediately after strenuous physical activity. Complete rehydration does not have to occur immediately after intense physical exertion. However, it is important the individual replaces lost sodium as soon as possible. The individual will be unable to retain water without proper sodium levels and will be unable to rehydrate completely. Within the scope of this invention, it is understood a person may also drink plain water to supplement the rehydration solution. The rehydration solution will supply the necessary electrolytes and other necessary chemical constituents. The body will completely hydrate over the course of time with proper internal sodium levels. Preferably, the participant will achieve 100 percent rehydration prior to participating in subsequent intense physical exertion.

The total sodium content of the solution should correspond to the sodium profile level. For illustrative purposes, the following example is provided. An individual with a sweat loss rate of 459 mg/L performs intense physical activity for 1.5 hours. The loss of sodium would be approximately 688 mg. The sodium loss would correspond to sodium profile level 2. The sodium content of the solution would optimally be about 600 mg. The sodium content should not deviate by less than 75 percent of the sodium profile level and not greater than 125 percent of the sodium profile level. More preferably, the sodium content should not deviate by less than 85 percent of the sodium profile level and not greater than 115 percent of the sodium profile level. The sodium in the rehydration solution is provided by sodium chloride. One of ordinary skill in the art will appreciate the appropriate concentrations of sodium in the rehydration solution. For example, concentrations exceeding 2000 mg/L may be unpalatable.

The sodium profile level can be adjusted by taking into account other sodium loss or gain. For instance, the urine collected during the determination of total water loss can be analyzed for sodium content. The loss of sodium found in the urine is added to the loss of sodium by perspiration. The result is an adjusted sodium profile level due to sodium loss from urine. Additionally, the dietary intake of sodium can be monitored post-physical activity. If only the sodium loss for urine or the sodium gained from dietary intake is accounted for, the sodium content of the solution should not deviate by less than 90 percent and not greater than 110 percent of the sodium profile level. If both the sodium loss from urine and the sodium gained from dietary intake are accounted for, the sodium content of the solution should not deviate by less than 95 percent and not greater than 105 percent of the sodium profile level.

The inventors have discovered the importance of chloride ion replacement in the prevention of cramping. Specifically, the chloride content of the rehydration solution should be maximized. Additional chloride is added to the solution by the addition of other salts. Suitable salts include lithium chloride, magnesium chloride and calcium chloride. Preferably, the additional chloride is added by the addition of magnesium chloride or calcium chloride. However, additional chloride should not be supplemented to a great extent, or at all, by potassium chloride. It has been discovered by the inventors that supplemental potassium is potentially harmful and not needed. The potassium serum levels were elevated during physical exertion when potassium was administered. Continued hyperkalemia could have long-term adverse effects of the kidneys and other organs. The potassium concentration should not exceed 25 mg/L. Preferably, the solution should contain no potassium. The rehydration solution should contain at minimum about 75 percent by weight of chloride compared to the chloride content of the perspiration generated by the person over the time period. More preferably, the rehydration solution should contain at minimum about 125 percent by weight of chloride compared to the chloride content of the perspiration generated by the person over the time period.

The solution should also contain a minimum of about 8 percent (w/v) carbohydrates. Preferably, the solution contains a minimum of about 10 percent (w/v) carbohydrates. Carbohydrates can aid in the absorption of fluid and sodium in the ilium. Suitable carbohydrates include fructose, dextrose, sucrose, maltose, lactose, tagatose, trehalose, isoglucose, mannitol, xylitol, lactibol, sorbitol, isomalt, maltitol, and the like. The carbohydrate may be of a single type or a combination thereof. Most preferably, the carbohydrate is dextrose.

The solution may also include dietary fiber. Suitable dietary fibers include one or more of the following dietary fibers, including dextrin, maltodextrin, inulins, cellulose, hemicellulose, oligofructose, lignin, pectin, psyllium, starch and or the like. Most preferably, the dietary fiber is maltodextrin.

The rehydration solution may also be provided to the participants as a set of unitary dosage rehydration compositions (such as a composition to be reconstituted). The unitary dosage rehydration compositions may comprise sodium, chloride, potassium, one or more carbohydrates, lactate, urea, calcium and magnesium. The weight percentage of sodium in each member of the set may differ by at most about 100 percent. More preferably, the weight percentage of sodium in each member of the set differs by at least about 20 percent. The weight percentage of chloride in each member of the set may exceed the weight percentage of sodium in that member by at least about 40 percent. The carbohydrate may include one or more of the following, fructose, dextrose, sucrose, maltose, lactose, tagatose, trehalose, isoglucose, mannitol, xylitol, lactibol, sorbitol, isomalt, or maltitol. Preferably, the set of unitary dosage rehydration compositions will contain no potassium. However, in accordance with this invention, a small amount of potassium may be present. For example, the set of unitary dosage rehydration compositions may contain up to about 0.05 percent (w/w) potassium.

Each member of the set being may be perceptually labeled to distinguish that member from the other members of the set by one of the human senses. For example, the container by be distinguished by size, shape, texture, color, taste, or smell.

The set of unitary dosage rehydration compositions may have at least 3 members. Preferably, the set should contain at least seven members. The member which contains the least amount of sodium content may have at least about 0.15 percent weight of sodium (grams sodium/grams unitary dosage). More preferably, the sodium content may have at least about 0.20 percent weight of sodium (grams sodium/grams unitary dosage). On the other hand, the member which contains the highest sodium content may have at least about 1.50 percent by weight of sodium (grams sodium/grams unitary dosage). More preferably, the member which contains the highest sodium content may have at least about 1.20 percent by weight of sodium (grams sodium/grams unitary dosage).

The unitary dosage rehydration compositions may also include dietary fiber. Suitable dietary fibers include one or more of the following dietary fibers, including dextrin, maltodextrin, inulins, cellulose, hemicellulose, oligofructose, lignin, pectin, psyllium, starch and or the like. Most preferably, the dietary fiber is maltodextrin.

In accordance with this invention, the members of the set correspond in sodium and chloride content to the sodium and chloride needs of corresponding groups of persons habituated to strenuous physical exertion over a time interval of such strenuous physical exertion.

The following provides an exemplary set of unitary dosages. Table 2 illustrates a set of five unitary dosage compositions to be prepared with 20 ounces (591.5 mL) of water. Each unitary dosage has a total mass of 80.0 g (containing 70.95 g of dextrose and 0 mg of potassium). The sodium content of the set is distributed to sufficiently populate the set. It will be understood by one of ordinary skill the set should be populated sufficiently to allow for administration of the unitary dosages to a variety of individuals with varying perspiration sodium content and perspiration rates. Within the scope of the invention, the members of the set may be expanded. For example, a set of unitary dosages may contain seven members wherein the members differ in sodium content by a difference to produce solutions of 300, 600, 900, 1200, 1500, 1800, and 2100 mg Na/L after dilution. On the other hand, a set of unitary dosages may contain seven members wherein the members differ in sodium content by a difference to produce solutions of 200, 400, 600, 800, 1000, 1200, and 1400 mg Na/L. It will be understood by one of ordinary skill the art the set of unitary dosages can vary by their sodium content and may encompass a variety of different ranges of sodium content so long as the range is sufficiently populated.

TABLE 2

| Level | Sodium concentration after dilution (mg/L) | Sodium content (mg) | Percent weight of sodium (%) | Chloride content (mg) | Percent weight of chloride (%) |
| --- | --- | --- | --- | --- | --- |
| 1 | 300 | 177 | 0.22 | 272 | 0.34 |
| 2 | 600 | 354 | 0.44 | 546 | 0.68 |
| 3 | 900 | 531 | 0.66 | 819 | 1.02 |
| 4 | 1200 | 708 | 0.89 | 1092 | 1.36 |
| 5 | 1500 | 885 | 1.11 | 1365 | 1.70 |

The following is a description of how an athletic trainer may employ the invention. Many professional athletes participate in strenuous physical activity prior to being acclimatized to a particular environment prior to their season (in what is commonly referred to as "training camp"). The athletic trainer needs to determine the perspiration rate and sodium content of the perspiration. This may be done prior to the commencement of training camp or at the beginning of training camp. The athletic trainer will accurately measure the weight of the athletes prior to intense physical exertion and then affix a suitable number of perspiration pads to the athlete. If this procedure is done prior to the commencement of training camp, the athletic trainer will have the athlete perform intense physical exertion (such as running on a tread mill or the like). Alternatively, this process may be performed during one of the first periods of physical exertion of training camp. After approximately 30 minutes, but prior to 60 minutes, the athletic trainer will collect the perspiration pads. The pads should be transferred to a sterile receptacle. The receptacle should also prevent evaporation and should be configured to easily remove the pads and all remnants of perspiration. Suitable receptacles include sealable vials or the like. The athlete is accurately weighed and the total water loss is determined in accordance with equation (1). The athletic trainer will transport the sealable vial to the appropriate location to assay for sodium. The athletic trainer then will do the typical water loss per hour and the sodium concentration of the athlete's perspiration. Upon determining these variables, the athletic trainer will monitor how long the athlete performs intense physical activity. With this information, the athletic trainer can provide a suitable rehydration solution.

The following example exemplifies the invention. A professional hockey player was followed over the course of 10 days in which the athlete participated in strenuous physical activity on five occasions. A particular athlete was 24 years old, 183 cm (72 inches) tall, and weighed 87.3 kg (192 lb.) prior to the first period of physical activity. Two days after the $5^{th}$ period of strenuous physical activity, the player weighed 81.8 kg (180 lb.). This indicates a fluid deficit of 5.5 L. Insufficient sodium consumption can result in the inability for proper rehydration.

It was determined the professional athlete had a sweat rate of 2 L/hour and a sodium loss of 90 mmol/L (2070 mg/L). During the typical period of intense physical exertion of three hours, the professional athlete would lose about 6 L of perspiration, 12.4 grams of sodium and 19.1 grams of chloride. The current invention will prevent such loss of fluid deficit over a period of time. In the instant example, the professional athlete should consume a minimum of 75 percent of his sodium loss (approximately 1550 mg Na/L or a total of 9.3 g of Na) and maximum of 125 percent of his sodium loss (approximately 2590 mg/L or a total of 15.5 g of Na) after participating in intense physical activity for three hours. The professional athlete should consume a minimum of 75% of his chloride loss (approximately 2393 mg/L or a total of 14.4 g of Cl). The athlete may be assigned to Level 5, 6, 7 or 8 (1500, 1800, 2100 or 2400). The professional athlete should consume a minimum of 50 percent of his water loss (3 L) and a maximum of 125 percent of his water loss (7.5 L). Within the scope of this invention, the athlete may be assigned to Level 5 (1500) and provided approximately 7 L of Level 5 solution which would contain a total of 10.5 g of Na and 16.2 g of Cl. This would equal approximately 12 unitary dosages (1 dosage=80.0 g per 591.5 mL of water). A person of ordinary skill in the art will appreciate the athlete may be assigned to the other levels and be provided the appropriate solution. Replenishing the sodium and water loss will allow the athlete to maintain his playing weight and perform at maximum performance Such regiment should be followed after intense physical exertion throughout the athlete's season.

The athletic trainer may also test and monitor athletes through training camp and their respective professional seasons. For example, monitoring of the athlete's weight may indicate proper sodium and water intake. A loss of weight could indicate sodium deficiency due to the athlete's inability to retain water. On the other hand, increased weight could indicate excess sodium intake. Furthermore, the athletic trainer may monitor the athlete's perspiration for the concentration of sodium. Any increase or decrease may lead to adjustment of the sodium level in which the athlete is assigned.

What is claimed:

1. A method for maintaining electrolyte balance and hydration in a person habituated to strenuous physical exertion comprising:
 a. assaying perspiration generated by the person under conditions of strenuous physical exertion to determine
  i. volume of perspiration as a function of duration of exertion; and
  ii. sodium content of the person's perspiration during strenuous physical exertion;
 b. assigning the person to one of a plurality of groups of individuals, each group differing in the amount of sodium present in the perspiration during strenuous physical exertion of individuals assigned to that group; and
 c. providing to the person after a period of strenuous physical activity a rehydration solution designed for individuals assigned to the group to which the person is assigned;
 d. the rehydration solution being provided
  i. in an amount comprising from about 50 volume percent to about 125 volume percent of the amount of perspiration generated by the person over the time period;
  ii. said solution having from about 75 percent to about 125 percent by weight of the sodium content of the perspiration generated by the person over the time period; and
  iii. said solution having at least about 75 percent by weight of chloride compared to the chloride content of the perspiration generated by the person over the time period.

2. The method of claim 1 wherein the rehydration solution being provided is in an amount comprising from about 65 volume percent to about 100 volume percent of the amount of perspiration generated by the person over the time period.

3. The method of claim 1 wherein the rehydration solution having from about 85 percent to about 115 percent by weight of the sodium content of the perspiration generated by the person over the time period.

4. The method of claim 1 wherein the rehydration solution having at least about 125 percent by weight of chloride compared to the chloride content of the perspiration generated by the person over the time period.

5. The method of claim 1 wherein the assaying further includes determination of the chloride content of the perspiration.

6. The method of claim 1 wherein the assaying further includes determination of the potassium content of the perspiration.

7. The method of claim 1 wherein the rehydration solution is prepared by dissolving a unitary dosage form of solids in water.

8. The method of claim 1 wherein the rehydration solution provided to the person is matched to the group to which he is assigned.

9. The method of claim 1 wherein a plurality of rehydration solutions or precursor solid dosage forms for preparing rehydration solutions are prepared, each matched to one of the groups.

10. The method of claim 1 wherein perspiration which is assayed is located on a plurality of locations on the body of the person.

11. The method of claim 1 wherein the perspiration is collected from about 30 minutes to 60 minutes after initiation of physical exertion.

12. The method of claim 1 wherein the rehydration solution further comprises at least one carbohydrate.

13. The method of claim 12 wherein the carbohydrate is fructose, dextrose, sucrose, maltose, lactose, tagatose, trehalose, isoglucose, mannitol, xylitol, lactibol, sorbitol, isomalt, maltitol, or a combination thereof.

14. A method for maintaining electrolyte balance and hydration in a person habituated to strenuous physical exertion comprising;
 a. determining total sodium loss of the person during a time period of strenuous physical exertion;
 b. providing to the person after the period of strenuous physical activity a rehydration solution, said solution comprising
  i. from about 75 percent to about 125 percent by weight of the sodium loss by the person over the time period;
  ii. less than 1 percent potassium compared to the weight of sodium; and
  iii. at least about 75 percent chloride by weight of the chloride content of the perspiration generated by the person over the time period.

15. The method of claim 14 wherein the rehydration solution is from about 85 percent to about 115 percent by weight of the sodium loss by the person over the time period.

16. The method of claim 14 wherein the rehydration solution is at least about 125 percent chloride by weight of the chloride content of the perspiration generated by the person over the time period.

17. The method of claim 14 wherein the rehydration solution is prepared by dissolving a unitary dosage form of solids in water.

18. The method of claim 14 wherein the rehydration solution further contains at least one carbohydrate.

19. The method of claim 18 wherein the carbohydrate is fructose, dextrose, sucrose, maltose, lactose, tagatose, trehalose, isoglucose, mannitol, xylitol, lactibol, sorbitol, isomalt, maltitol, or a combination thereof.

20. A method for maintaining electrolyte balance and hydration in a person habituated to strenuous physical exertion comprising:
 a. assaying perspiration generated by the person under conditions of strenuous physical exertion to determine
  i. volume of perspiration as a function of duration of exertion; and
  ii. sodium content of the perspiration
 b. assaying urine generated by the person during strenuous physical exertion to determine
  i. volume of urine lost and
  ii. sodium content of the urine;
 c. determining a total loss of sodium by the person over the time period;
 d. assigning the person to one of a plurality of groups, each group differing in the amount of sodium present in the perspiration and urine of individuals assigned to the group; and
 e. providing to the person after a period of strenuous physical activity a rehydration solution
  i. in an amount comprising from about 50 volume percent to about 100 volume percent of the amount of perspiration generated by the person over the time period;
  ii. said solution having from about 85 percent to about 115 percent of total loss of sodium by the person over the time period; and
  iii. said solution having at least about 75 percent by weight of chloride compared to the chloride content of the perspiration generated by the person over the time period.

21. The method of claim 20 wherein the rehydration solution being provided is in an amount comprising from about 65 volume percent to about 100 volume percent of the amount of perspiration generated by the person over the time period.

22. The method of claim 21 wherein the rehydration solution having from about 90 percent to about 110 percent of total loss of sodium by the person over the time period.

23. The method of claim 21 wherein the rehydration solution having at least about 125 percent by weight of chloride compared to the chloride content of the perspiration generated by the person over the time period.

24. The method of claim 21 wherein the assaying further includes determination of the chloride content of the perspiration.

25. The method of claim 21 wherein the assaying further includes determination of the potassium content of the perspiration.

26. The method of claim 21 wherein the rehydration solution is prepared by dissolving a unitary dosage form of solids in water.

27. The method of claim 21 wherein the rehydration solution provided to the person is matched to the group to which he is assigned.

28. The method of claim 21 wherein a plurality of rehydration solutions are extant, each matched to one of the groups.

29. The method of claim 21 wherein perspiration which is assayed is located on a plurality of locations on the body of the person.

30. The method of claim 21 wherein the perspiration is collected from about 40 minutes to 60 minutes after initiation of physical exertion.

31. The method of claim 21 wherein the rehydration solution contains a carbohydrate or carbohydrates.

32. The method of claim 31 wherein the carbohydrate is fructose, dextrose, sucrose, maltose, lactose, tagatose, trehalose, isoglucose, mannitol, xylitol, lactibol, sorbitol, isomalt, maltitol, or combination thereof.

33. A method for maintaining electrolyte balance and hydration in a person habituated to strenuous physical exertion comprising:
 a. assaying perspiration generated by the person under conditions of strenuous physical exertion to determine
  i. volume of perspiration as a function of duration of exertion; and
  ii. sodium content of the perspiration
 b. determining the dietary intake of sodium by the person;
 c. determining a total loss of sodium by the person over the time period;
 d. assigning the person to one of a plurality of groups, each group differing in the amount of sodium present in the perspiration and the dietary intake of individuals assigned to the group; and e. providing to the person after a period of strenuous physical activity a rehydration solution
   i. in an amount comprising from about 50 volume percent to about 125 volume percent of the amount of perspiration generated by the person over the time period;
   ii. said solution having from about 85 percent to about 115 percent of the total loss of sodium by the person over the time period; and
   iii. said solution having at least about 75 percent by weight of chloride compared to the chloride content of the perspiration generated by the person over the time period.

34. The method of claim 33 wherein the rehydration solution being provided is in an amount comprising from about 65 volume percent to about 100 volume percent of the amount of perspiration generated by the person over the time period.

35. The method of claim 33 wherein the rehydration solution having from about 90 percent to about 110 percent of the total loss of sodium by the person over the time period.

36. The method of claim 33 wherein the rehydration solution having at least about 125 percent by weight of chloride compared to the chloride content of the perspiration generated by the person over the time period.

37. The method of claim 33 wherein the rehydration solution is prepared by dissolving a unitary dosage form of solids in water.

38. The method of claim 33 wherein the rehydration solution provided to the person is matched to the group to which he is assigned.

39. The method of claim 33 wherein a plurality of rehydration solutions are extant, each matched to one of the groups.

40. The method of claim 33 wherein perspiration which is assayed is located on a plurality of locations on the body of the person.

41. A method for maintaining electrolyte balance and hydration in a collection of persons, each of whom is habituated to strenuous physical exertion comprising:
   a. assaying perspiration generated by each person of the group under conditions of strenuous physical exertion to determine
      i. volume of perspiration as a function of duration of exertion; and
      ii. sodium content of the perspiration
   b. assigning each person to one of a plurality of groups, each group differing in the amount of sodium present in the perspiration of individuals assigned to the group; and
   c. providing to at least some of the persons after a period of strenuous physical activity a rehydration solution
      i. in an amount comprising from 50 volume percent to 125 volume percent of the amount of perspiration generated by the person over the time period;
      ii. said solution having from about 75 percent to about 125 percent of the sodium content of the perspiration generated by the person over the time period;
      iii. said solution having at least about 110 percent by weight of chloride compared to the chloride content of the perspiration generated by the person over the time period.

42. The method of claim 41 wherein the rehydration solution being provided is in an amount comprising from about 65 volume percent to about 100 volume percent of the amount of perspiration generated by the person over the time period.

43. The method of claim 41 wherein the rehydration solution said solution having from about 85 percent to about 115 percent of the sodium content of the perspiration generated by the person over the time period.

44. The method of claim 41 wherein the rehydration solution having at least about 125 percent by weight of chloride compared to the chloride content of the perspiration generated by the person over the time period.

45. A set of unitary dosage rehydration compositions, each member of the set comprising sodium and chloride;
   a. the weight percentage of sodium in each member of the set differing from the weight percentage of sodium in the other members by a difference such that the distribution of the members of the set sufficiently populate the set;
   b. the weight percentage of chloride in each member of the set exceeding the weight percentage of sodium in that member by at least about 40 percent; and
   c. each member of the set being perceptually labeled to distinguish that member from the other members of the set by one of the human senses.

46. The set of claim 45 wherein the set comprises five members with the set populated with members that have a weight percentage of sodium of about 0.2 percent, 0.4 percent, 0.7 percent, 0.9 percent and 1.11 percent.

47. The set of claim 45 wherein at least one of the members further comprises up to about 0.05 percent by weight potassium.

48. The set of claim 45 wherein at least one of the members further comprises at least one carbohydrate.

49. The set of claim 48 wherein the carbohydrate is fructose, dextrose, sucrose, maltose, lactose, tagatose, trehalose, isoglucose, mannitol, xylitol, lactibol, sorbitol, isomalt, maltitol, or a combination thereof.

50. The set of claim 45 wherein at least one of the members further comprises at least one of potassium, carbohydrate, lactate, urea, calcium, and magnesium.

51. The set of claim 45 wherein the set has at least seven members, the member having the least sodium content having less than about 75 percent by weight of sodium in perspiration, and the member having the highest sodium content having at least about 125 percent by weight of sodium in perspiration.

52. The set of claim 45 wherein the members of the set correspond in sodium and chloride content to the sodium and chloride needs of corresponding groups of persons habituated to strenuous physical exertion over a time interval of such strenuous physical exertion.

53. The set of claim 45 wherein the labeling is in the shape of a container for each member of the set.

54. The set of claim 45 wherein the labeling is in the color of a container for each member of the set.

55. The set of claim 45 wherein the labeling is in the taste or smell of each member of the set.

* * * * *